United States Patent [19]
Holland

[11] 3,953,595
[45] Apr. 27, 1976

[54] SUBSTITUTED BENZOIC ACID HYPOLIPEMIC AGENTS

[75] Inventor: Gerald Fagan Holland, Old Lyme, Conn.

[73] Assignee: Pfizer Inc., New York, N.Y.

[22] Filed: May 3, 1974

[21] Appl. No.: 466,774

Related U.S. Application Data

[62] Division of Ser. No. 304,528, Nov. 7, 1974, which is a division of Ser. No. 155,209, June 21, 1971.

[52] U.S. Cl. .............................. 424/230; 421/317
[51] Int. Cl.² ....................................... A61K 31/19
[58] Field of Search ........................... 424/319, 230

[56] References Cited
UNITED STATES PATENTS

| | | | |
|---|---|---|---|
| 3,594,478 | 7/1971 | Brandstrom et al. | 260/330.5 |
| 3,729,508 | 4/1973 | Ziegler et al. | 260/470 |

*Primary Examiner*—Jerome D. Goldberg
*Attorney, Agent, or Firm*—Connolly and Hutz

[57] ABSTRACT

Polysubstituted benzoic acids, and their use in mammals as hypolipemic agents.

2 Claims, No Drawings

SUBSTITUTED BENZOIC ACID HYPOLIPEMIC AGENTS

CROSS REFERENCE TO RELATED APPLICATIONS

This application is a division of application Serial No. 304,528 filed Nov. 7, 1972, which, in turn, is a division of application Ser. No. 155,209 filed June 21, 1971.

BACKGROUND OF THE INVENTION

Atherosclerosis, a form of arteriosclerosis, is characterized by deposition of lipids in the aorta and in the coronary, cerebral and peripheral arteries of the lower extremities. As these masses increase in size, the risk of thrombosis and the ensuing occlusion arises.

Although the etiology of this disease is not fully understood, it has been found that those afflicted with atherosclerosis exhibit elevated levels of plasma lipoprotein, of which cholesterol and triglycerides are the major constituents. In addition to the recommendation that dietary habits leading to lower $\beta$-lipoprotein levels be observed, various therapeutic agents such as estrogens, thyroxine analogs, sitosterol preparations and, more recently, Atromid-S (ethyl p-chlorophenoxyisobutyrate) have been used to lower cholesterol levels in individuals prone to the condition.

It has now been found that benzoic acids, and more particularly a series of polysubstituted benzoic acids are effective in reducing plasma lipid levels and can be expected to be useful in the treatment of atherosclerosis and related cardiovascular diseases associated with elevated lipid levels.

Benzoic acid derivatives have been known in the chemical literature for some time and have been reported to possess varied utilities, the most common of which is as intermediates leading to more complicated and diverse chemical structures. For example, S-phenacylthiosalicylic acids are reported, Netherlands Specification 6,607,608, to be useful in the synthesis of benzothiophenes reported to be valuable because of their analgetic, antipyretic, antiinflammatory, antitussive, local anesthetic, antispasmodic, and antihistaminic activity.

Benzoic acid derivatives are utilized in the synthesis of tricyclic dibenz[b,e]oxepines (Collect. Czech. Chem. Commun., 32, 3448, 1967; C.A., 68, 29677r, 1968) and dibenzo[b,f]thiepins (Collect. Czech. Chem. Commun., 33, 1852, 1968; C.A., 69, 86950u, 1968), useful as neurotropic and psychotropic agents.

Quinuclidinyl esters, claimed in U.S. Pat. No. 3,405,134 as central nervous stimulants, utilizes m-benzyloxybenzoic acid in the preparation of final products.

Baker, et al., J. Med. Chem., 10, 1129 (1967), has recently shown that certain phenacyloxy and acetonyloxy derivatives of benzoic acid are inhibitors of $\alpha$-chymotrypsin.

Recently, m-fluorobenzoic acid has been reported, Belgium Patent 724,121, to possess analgesic, antipyretic and hypolipemic activity.

Summary of the Invention

The hypolipemic agents of this invention are represented by the formula:

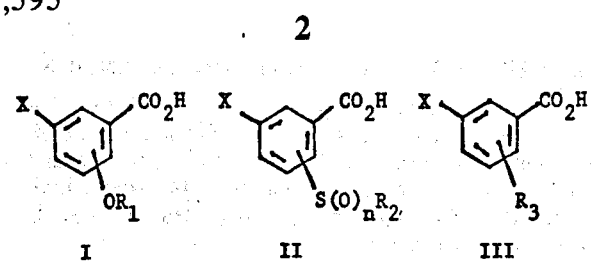

and the pharmaceutically acceptable basic salts thereof, where:

X is selected from the group consisting of fluorine, chlorine, bromine, methyl, methoxy and trifluoromethyl;

$R_1$ is selected from the group consisting of methyl, benzyl, substituted benzyl where said substituent is selected from the group consisting of fluorine, chlorine, methyl, methoxy, trifluoromethyl and 3,4-dimethoxy and acylmethyl of the formula

where R is selected from the group consisting of alkyl containing from 1 to 4 carbon atoms and phenyl and substituted phenyl where said substituent is selected from the group consisting of fluorine, chlorine, methyl, trifluormethyl and methoxy;

$R_2$ is selected from the group consisting of methyl, 2-hydroxyethyl, ally, methallyl, crotyl and acylmethyl of the formula

where R is selected from the group consisting of alkyl containing from 1 to 4 carbon atoms and phenyl and substituted phenyl wherein said substituent is selected from the group consisting of fluorine, chlorine, methyl, trifluoromethyl and methoxy;

n is an integer from 0 to 2; and $R_3$ is selected from the group consisting of fluorine, chlorine, bromine and methyl.

Of particular interest are compounds of formula I where X is chlorine and $R_1$ is benzyl, 3,4-dimethoxybenzyl or acylmethyl of the formula

where R is alkyl containing from 1 to 4 carbon atoms, and where X is trifluoromethyl and $R_1$ is methyl or benzyl.

A second group of prepared compounds are those of formula II where X is trifluoromethyl, n is O and $R_2$ is allyl, methallyl, or phenacyl, and where X is chlorine, n is O and $R_2$-hydroxyethyl or phenacyl.

Also considered within the purview of this invention are compounds of formula I where $R_1$ is phenyl and phenyl substituted by simple substituents usually found on aromatic rings, i.e., alkyl, halo, alkoxy, etc.

DETAILED DESCRIPTION OF THE INVENTION

In accordance with the process employed for synthesizing substituted benzoic acids of formulae I and II, wherein X is fluorine, chlorine, bromine, methyl and methoxy, n is O and $R_1$ and $R_2$ are as previously indicated, the following scheme, where Hal- is suitable halogen, is illustrative:

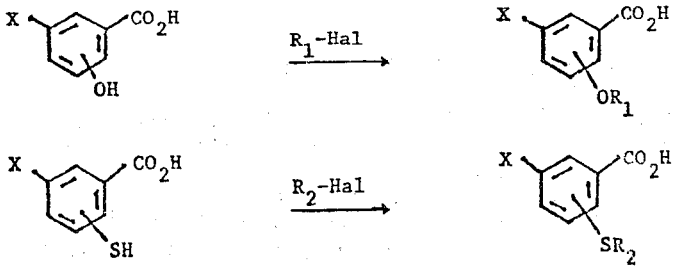

Both the above illustrated reactions are conducted under similar conditions well known to those skilled in the art and comprises heating a basic salt of the phenol or thiophenol with at least an equimolar amount of the appropriate halide, $R_1$-Hal or $R_2$-Hal, in a reaction-inert solvent.

For convenience, the basic salt of the phenol or thiophenol, the preferred salt being sodium, is generated in situ employing one or more of the bases sodium hydride, sodium methoxide, sodium hydroxide or sodium carbonate. At least one equivalent of said base is used, with as much as a 100% excess.

The solvent can vary considerably in nature and can comprise one or more of those selected from dimethylsulfoxide, dimethylformamide, hexamethylphosphoramide, acetone, ethanol, methanol and water.

In practice, a solution or suspension of the requisite phenol or thiophenol in a reaction-inert solvent is treated with one or more of the aforementioned bases followed by the addition of the appropriate halide, $R_1$-Hal or $R_2$-Hal. In general, it is advantageous to conduct the reaction at elevated temperatures, the preferred range being from 75°–150° C. Reaction time is not critical and is dependent on temperature, cooncentration and reactivity of the starting reagents. Times of 1–12 hours have generally been adequate to provide the desired products in good to moderate yields.

A convenient method for isolation of the product comprises dilution of the cooled reaction mixture with water followed by acidification with 6N hydrochloric acid. The resulting precipitate is then filtered, dried and recrystallized from a suitable solvent.

Starting phenols and thiophenols wherein X is trifluoromethyl and the hydroxyl or mercapto group to be alkylated are ortho or para to said trifluoromethyl moiety represent a special case since said phenol or thiophenols cannot be alkylated under the aforedescribed basic reaction conditions. Compounds of the present invention related to I and II wherein X is trifluoromethyl and $R_1$O- or $R_2$S- are ortho or para to said trifluoromethyl substituent are prepared by displacement of an aromatic halogen ortho or para to the trifluoromethyl substituent by the requisite alcohol, $R_1$OH, or mercaptan $R_2$SH. Further, it is frequently advantageous to employ, instead of the trifluoromethyl substituted halobenzoic acid, the corresponding trifluoromethyl substituted halobenzonitrile, which, after the reaction is complete, can be suitably hydrolyzed to the benzoic acid.

The above-described reaction is generally carried out by contacting the appropriate trifluoromethyl-halobenzoic acid or nitrile with at least an equimolar amount of the requisite alcohol or mercaptan, plus as much as a 10–50% excess, in an aprotic solvent such as dimethylformamide, dimethylsulfoxide or hexamethylphosphoramide and employing from 1 to 2 molar equivalents of a base such as sodium methoxide or sodium hydride. Such reaction is generally conducted at elevated temperatures of from 80°–150° C. for 2–10 hours. The desired product is isolated by dilution of the reaction mixture with water followed by adjustment of the pH to 3 with 6N hydrochloric acid.

In those instances wherein the nitrile is employed, the benzoic acid is obtained by subsequent hydrolysis of the product employing aqueous ethanolic sodium hydroxide at steam bath temperatures and reaction times of 12 to 24 hours.

Those trifluoromethyl benzoic acid congeners wherein the hydroxy or mercapto are situated meta to the trifluoromethyl substituent can be alkylated directly by the aforedescribed procedure.

The requisite hydroxybenzoic acids employed as the starting materials leading to compounds of formula I are either available as commercial reagents or are well known in the chemical literature to those skilled in the art.

The corresponding mercaptobenzoic acids used as the starting compounds for the preparation of those congeners related to formula II are either commercially available or can be synthesized either from the corresponding hydroxybenzoic acid employing the method of Newman, et al., J. Org. Chem., 31, 3980 (1966), which teaches the acylation of a phenol with dimethylthiocarbamyl chloride, thermal rearrangement to the S-aryl dimethylthiocarbamate and subsequent hydrolysis to the thiophenol; or from the corresponding aminobenzoic acid using the procedure of Tarbell, et al., "Organic Synthesis," Coll. Vol. III, John Wiley & Sons, Inc., New York, New York, 1955, page 809, which teaches the reaction of a diazonium salt with potassium ethyl xanthate followed by hydrolysis of the intermediate to the thiophenol.

The appropriate trifluoromethyl halobenzoic acid and benzonitriles are compounds fully disclosed in the chemical literature.

Regarding the alkylating reagents employed in the process leading to compounds of the present invention, allyl, crotyl, methallyl and certain phenacyl and benzyl halides are commercially available. Those benzyl halides not available as commercial chemicals can easily be prepared by those skilled in the art according to the methods as taught by Fuson and McKeever, "Organic Reactions" Vol. I, John Wiley & Sons, Inc., New York, New York, 1954, Chapter 3; and Wagner and Zook, "Synthetic Organic Chemistry," John Wiley & Sons, Inc., New York, New York, 1956, Chapter 4. Phenacyl halides and α-halomethyl alkyl ketones are synthesized according to the methods as outlined by Wagner & Zook, "Synthetic Organic Chemistry," John Wiley & Sons, Inc., New York, New York, 1956, Chapter 4.

The requisite benzyl alcohols are either commercial chemicals or are prepared by a lithium aluminum hydride reduction of the corresponding alkyl benzoate according to the methods outlined by Brown, "Organic Reactions," Vol. 6, John Wiley & Sons, Inc., New York, New York, '1951, Chapter 10. The requisite acylcarbinols,

are prepared via hydrolysis of the corresponding acylmethyl halides according to the procedure of Straus, Ann., 393, 331 (1912), while the corresponding mercaptomethyl ketones,

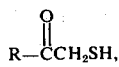

are synthesized from the appropriate acylmethyl halides according to the methods reported by Reid, "Organic Chemistry of Bivalent Sulphur," Vol. I, Chemical Publishing Co., Inc., New York, New York, 1958, Chapter 4, page 390.

The sulfoxides and sulfones of formula II, wherein n = 1 or 2, are synthesized by oxidation, employing standard oxidizing agents such as hydrogen peroxide or potassium permanganate.

The structurally novel hypolipemic compounds of the present invention comprise those of formula I and their pharmaceutically acceptable basis salts, wherein X is selected from the group consisting of fluorine, chlorine, bromine and trifluoromethyl and $R_1$ is selected from the group consisting of benzyl and substituted benzyl wherein said substituent is selected from the group consisting of fluorine, chlorine, methyl, methoxy, trifluoromethyl and 3,4-dimethoxy and acylmethyl of the formula

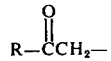

wherein R is selected from the group consisting of alkyl containing from 1 to 4 carbon atoms and phenyl and substituted phenyl wherein said substituent is selected from the group consisting of fluorine, chlorine, methyl, methoxy and trifluoromethyl.

Also structurally novel are hypolipemic agents of the present invention represented by formula II and their pharmaceutically acceptable basic salts, wherein Y is selected from the group consisting of fluorine, bromine and trifluoromethyl; $R_2$ is selected from the group consisting of allyl, methallyl, crotyl and acylmethyl of the formula

wherein R is selected from the group consisting of alkyl containing from 1 to 4 carbon atoms and phenyl and substituted phenyl wherein said substituent is selected from the group consisting of fluorine, chlorine, methyl, trifluoromethyl and methoxy; and n is an integer from 0 to 2.

Compounds of the present invention of formula III and their pharmaceutically acceptable basic salts are all either commercially available or described in the chemical literature and are synthesized according to known standard procedures, for example, those outlined and reported by Moffett, et al., J. Med. Chem., 11, 1020 (1968), Karler, et al., Arch. Intern. Pharmacodyn., 173, 270 (1968), Hansch, et al., Biochem. Pharmacol., 19, 2193 (1970), Muir, et al., Plant Physiol., 26, 369 (1951), Zimmerman, et al., Contr. Boyce Thompson Inst., 12, 321 (1942) and in "Dictionary of Organic Compounds," Oxford University Press, New York, New York, 1965, Volumes 1–5.

As has been previously noted, a characteristic feature of the acidic compounds of the instant invention is their ability to form basic salts. Acid congeners of the present invention are converted to basic salts by the interaction of said acid with an appropriate base in an aqueous or non-aqueous medium. Said basic reagents suitably employed in the preparation of said salts can vary in nature, and are meant to contemplate such bases as organic amines, ammonia, alkali metal hydroxides, carbonates, bicarbonates, hydrides and alkoxides, as well as alkali earth metal hydroxides, hydrides, alkoxides and carbonates. Representative of such bases are ammonia, primary amines such as n-propylamine, n-butylamine, aniline, cyclohexylamine, benzylamine, p-toluidine, ethylamine, octylamine, tertiary amines such as diethylaniline, N-methylpyrrolidine, N-methylmorpholine and 1,5-diazabicyclo-[4,3,0]-nonene; sodium hydroxide, potassium hydroxide, ammonium hydroxide, sodium ethoxide, potassium methoxide, magnesium hydroxide, calcium hydride and barium hydroxide.

In the utilization of the chemotherapeutic activity of those compounds of the present invention which form basic salts, it is preferred, of course, to use pharmaceutically acceptable salts. Although water-insolubility, high toxicity, or lack of crystalline nature may make some salt species unsuitable or less desirable for use as such in a given pharmaceutical application, the water insoluble or toxic salts can be converted to the corresponding acids by decomposition of the salts as described above, or alternately they can be converted to any desired pharmaceutically acceptable basic salt. The said pharmaceutically acceptable salts preferred are those wherein the cation is ammonium, sodium or potassium.

As previously indicated, the benzoic acids of the present invention are all readily adapted to therapeutic use as hypolipemic agents in mammals. Outstanding for their effectiveness in this regard include the following agents: 2-benzyloxy-5-trifluoromethylbenzoic acid, 2-benzyloxy-5-chlorobenzoic acid, 2-(3,4-dimethoxybenzyloxy)-5-chlorobenzoic acid, 2-acetonyloxy-5-chlorobenzoic acid, 2-methoxy-5-trifluoromethylbenzoic acid, 3-methoxy-5-trifluoromethylbenzoic acid, 2-allylthio-5-trifluoromethylbenzoic acid, 2-methallylthio-5-trifluoromethylbenzoic acid, 3-phenacylthio-5-trifluoromethylbenzoic acid, 2-(2-hydroxyethylthio)-5-chlorobenzoic acid and 2-phenacylthio-5-chlorobenzoic acid.

The products of the invention are tested in vivo for hypolipemic activity in rats. Groups, each comprising 4 animals, of normal Sprague-Dawley (Charles River) male rats weighing from 160 to 220 grams are fed rat chow containing the compound under test for two overnight feeding periods. On the morning of the third day the animals are anesthetized and bled from the abdominal aorta. The total plasma cholesterol is then determined by the method of J. J. Carr and I. J. Drekter, reported in Clin. Chem., 2, 353 (1956). Most of the tests are conducted at a feed concentration of 0.15 to 0.25 weight percent of the compound under test, but lower levels, 0.01 to 0.10 weight percent, are employed in some instances where particularly high potency is anticipated. The plasma cholesterol level of the treated animals is found to be significantly reduced with compared to animals not receiving the test compound.

This pharmacological test for measuring hypocholesteremic activity is a reliable indication that similar activity in humans can be expected because those compounds effective in the rat which have been tested in humans have demonstrated similar activity. p-Chlorophenoxyisobutyric acid, ethyl ester, marketed as Atromid-S, a well-known and clinically effective hypocholesteremic agent, causes a 30–35% cholesterol fall in the rat test when administered at a level of 0.25% in the feed.

Although the use of the present invention is directed toward the treatment of mammals in general, the preferred subject is humans. In determining an efficacious dose for human therapy, results of animal testing are frequently extrapolated and a correlation is assumed between animal test behavior and proposed human dosage. When a commercially employed standard is available, the dose level of the clinical candidate in humans is frequently determined by comparison of its performance with the standard in an animal test. For example, Atromid-S is employed as a standard hypolipemic agent and is administered to humans at the rate of 2.0 g. daily in individual doses. It is assumed, then, that if compounds of the present invention have activity comparable to Atromid-S in the test assay, that similar doses will provide comparable responses in humans.

Obviously, the physician will ultimately determine the dosage which will be most suitable for a particular individual, and it will vary with the age, weight and response of the particular patient as well as with the nature and extent of the symptoms and the pharmacodynamic characteristics of the particular agent to be administered. Generally, small doses will be administered initially, with a gradual increase in the dosage until the optimum level is determined. It will often be found that when the composition is administered orally, larger quantities of the active ingredient will be required to produce the same level as produced by a small quantity administered parenterally.

Having full regard for the foregoing factors it is considered that an effective daily dosage of the compounds of the present invention in humans will generally range from 0.3 to 5 g. per day in single or divided doses. These values are illustrative, and there may, of course, be individual cases where higher or lower dose ranges are merited.

The benzoic acids of this invention can be administered either alone, or, preferably, in combination with a pharmaceutically acceptable carrier. They may be combined with various pharmaceutically acceptable, inert carriers in the form of tablets, capsules, lozenges, troches, powders, aqueous suspensions or solutions, elixirs, syrups and the like. Suitable carriers include solid diluents or aqueous media and non-toxic organic solvents. The oral pharmaceutiucal compositions of this invention may be suitably sweetened and flavored by means of various agents commonly employed for such a purpose.

For parenteral administration, solutions or suspensions of the herein described benzoic acids in sesame or peanut oil or in aqueous propylene glycol solutions can be employed, as well as sterile aqueous solutions of the corresponding water-soluble salts. Such solutions are suitable for intramuscular and subcutaneous administration. Sterile aqueous solutions are additionally useful for intravenous injection, provided that their pH is suitably adjusted and buffered, if necessary, and the liquid diluent rendered isotonic with saline or glucose.

The herein disclosed compounds may also be useful in other aspects of abnormal metabolism, the latter possibly accounting for clinical problems in diabetes, pancreatitis, coronary heart disease, and cerebrovascular disease. Hence the ability of polysubstitutedbenzoic acids of this invention to regulate lipid metabilism might find utility in the treatment of said disease.

Also considered within the scope of the present invention are compounds related to formula III wherein $R_3$ is amino or amino derivatives, e.g., mono- and disubstituted amine, urea or acylamine; and X is as previously indicated.

The following examples are provided solely for the purpose of illustration and are not to be construed as limitations of this invention, many variations of which are possible without departing from the spirit or scope thereof.

EXAMPLE 1

3-Benzyloxy-5-chlorobenzoic Acid

To a solution of 173 mg. (1 m mole) of 3-hydroxy-5-chlorobenzoic acid in 2 ml. of dimethylformamide is added 85 mg. (2 m moles) of 56.6% sodium hydride in an oil suspension. After ten minutes, the resulting suspension is treated with 130 mg. (1 m mole) of benzyl chloride and the mixture heated to 100° C. for one hour. The reaction mixture is then cooled, diluted with 5 ml. of water, and extracted with ether. The aqueous phase is separated, acidified with 6N hydrochloric acid and the product extracted with ether. The ether solvent is removed in vacuo and the residual product triturated with water and filtered. The dried product is sublimed at 125° C. and 0.02 mm of pressure to provide 50 mg. of the desired produce, m.p. 127–129° C.

Anal. Calcd. for $C_{14}H_{11}O_3Cl$: C, 64.00; H, 4.22. Found: C, 64.05; H, 4.31.

EXAMPLE 2

2-(3,4-Dimethoxybenzyloxy)-5-chlorobenzoic Acid

To a suspension resulting from 5.15 g. (0.03 mole) of 5-chlorosalicylic acid and 2.5 g. (0.6 mole) of sodium hydride (56.6% oil dispersion) in 50 ml. of dimethylformamide is added 11 g. ((0.065 mole) of 3,4-dimethoxybenzyl chloride and the mixture heated to 100°–107° C. for 40 minutes. The reaction mixture is cooled, diluted with 150 ml. of water and extracted with ether. The ether layer is washed with 1N sodium hydroxide solution, water and finally evaporated to dryness. The residual product, 3,4-dimethoxybenzyl 2-(3,4-dimethoxybenzyloxy)-5-chlorosalicylate is triturated with isopropanol, 7.5 g., m.p. 70°–83° C. A small sample is recrystallized from isopropanol, m.p. 90°–91.5° C.

Anal. Calcd. for $C_{25}H_{25}O_7Cl$: C, 63.49; H, 5.33. Found: C, 63.84; H, 5.43.

The above intermediate, 7.5 g. (15.8 m moles) in 50 ml. of acetone is treated with 50 ml. of 1N aqueous sodium hydroxide solution and 25 ml. of methanol and the solution heated on a steam bath for 3–4 minutes and stirred at room temperature for 15 minutes. Twenty-five milliliters of water is added and the acetone and methanol are removed under reduced pressure. The aqueous solution is extracted with ether and finally acidified with 6N hydrochloric acid. The resulting precipitate is filtered and dried, 4.8 g., m.p. 101°–105° C. The desired product is purified by recrystallization from methanol containing a small amount of methylene chloride, m.p. 110°–112° C.

Anal. Calcd. for $C_{16}H_{15}O_5Cl$: C, 59.54; H, 4.68. Found: C, 59.60; H, 4.86.

EXAMPLE 3

Following the procedure of Example 1 or Example 2, and starting with the appropriate hydroxybenzoic acid and benzyl halide, the following congeners are synthesized:

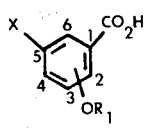

| X | $R_1$ | Position of Substituent-$CR_1$ | Procedure |
|---|---|---|---|
| F | $C_6H_5CH_2-$ | 2 | Example 2 |
| F | $C_6H_5CH_2-$ | 4 | Example 2 |
| F | $4\text{-}ClC_6H_4CH_2-$ | 3 | Example 1 |
| F | $2\text{-}FC_6H_4CH_2-$ | 2 | Example 2 |
| F | $3\text{-}CF_3C_6H_4CH_2-$ | 4 | Example 2 |
| F | $2\text{-}ClC_6H_4CH_2-$ | 3 | Example 1 |
| F | $4\text{-}CH_3C_6H_4CH_2-$ | 6 | Example 2 |
| F | $4\text{-}CH_3OC_6H_4CH_2-$ | 6 | Example 2 |
| F | $3\text{-}BrC_6H_4CH_2-$ | 2 | Example 2 |
| F | $4\text{-}BrC_6H_4CH_2-$ | 3 | Example 1 |
| F | $3\text{-}CH_3OC_6H_4CH_2-$ | 2 | Example 2 |
| Cl | $C_6H_5CH_2-$ | 2 | Example 2 |
| Cl | $C_6H_5CH_2-$ | 6 | Example 2 |
| Cl | $4\text{-}ClC_6H_4CH_2-$ | 3 | Example 1 |
| Cl | $4\text{-}FC_6H_4CH_2-$ | 2 | Example 2 |
| Cl | $4\text{-}FC_6H_4CH_2-$ | 4 | Example 2 |
| Cl | $4\text{-}CH_3C_6H_4CH_2-$ | 3 | Example 1 |
| Cl | $4\text{-}CH_3OC_6H_4CH_2-$ | 3 | Example 1 |
| Cl | $2\text{-}BrC_6H_4CH_2-$ | 6 | Example 2 |
| Cl | $3\text{-}CF_3C_6H_4CH_2-$ | 2 | Example 2 |
| Cl | $4\text{-}FC_6H_4CH_2-$ | 2 | Example 2 |
| Br | $C_6H_5CH_2-$ | 2 | Example 2 |
| Br | $C_6H_5CH_2-$ | 3 | Example 1 |
| Br | $3,4\text{-}(CH_3O)_2C_6H_3CH_2-$ | 2 | Example 2 |
| Br | $3,4\text{-}(CH_3O)_2C_6H_3CH_2-$ | 4 | Example 2 |
| Br | $4\text{-}FC_6H_4CH_2-$ | 3 | Example 1 |
| Br | $4\text{-}FC_6H_4CH_2-$ | 6 | Example 2 |
| Br | $3\text{-}CF_3C_6H_4CH_2-$ | 2 | Example 2 |
| Br | $4\text{-}CH_3OC_6H_4CH_2-$ | 2 | Example 2 |
| Br | $4\text{-}CH_3C_6H_4CH_2-$ | 2 | Example 2 |
| Br | $4\text{-}CH_3C_6H_4CH_2-$ | 4 | Example 2 |
| Br | $4\text{-}CH_3C_6H_4CH_2-$ | 3 | Example 1 |

EXAMPLE 4

2-Benzyloxy-5-trifluoromethylbenzoic Acid

To a solution of 10.8 g. (0.1 mole) of benzyl alcohol in 50 ml. of dimethylsulfoxide is added 4.2 g. (0.1 mole) of a 56.6% suspension of sodium hydride in oil, and the mixture stirred until the evolution of hydrogen ceases. 4-Chloro-3-cyanobenzotrifluoride (18.6 g.; 0.09 mole) is added and the resulting mixture heated 3–4 hours at steam bath temperatures. The reaction is cooled, diluted with 200 ml. of water and the resulting precipitate filtered and dried. The intermediate, 4-benzyloxy-3-cyanobenzotrifluoride, is recrystallized from isopropanol, 10.8 g., m.p. 69°–70.5° C.

To 10 ml. of ethanol containing 4 ml. of 5N aqueous sodium hydroxide solution is added 600 mg. of the above intermediate and the resulting solution heated to 90° C. overnight. The reaction mixture is cooled, extracted with ether, and the aqueous layer acidified with 12N hydrochloric acid. The precipitate which forms is filtered, washed with water and dried, 570 mg., m.p. 92°–94° C. A small sample is recrystallized for analysis from ether-hexane, m.p. 94.5°–96° C.

Anal. Calcd. for $C_{15}H_{11}O_3F_3$: C, 60.81; H, 3.74. Found: C, 60.64; H, 3.81.

EXAMPLE 5

3-Benzyloxy-5-trifluoromethylbenzoic Acid

To a solution resulting from 206 mg. (1 m mole) of 3-hydroxy-5-trifluoromethylbenzoic acid* and 85 mg. (2 m moles) of a 56.6% oil suspension of sodium hydride in 2 ml. of dimethylsulfoxide is added 127 mg. (1 m mole) of benzyl chloride and the reaction mixture heated to 90° C. for 1–2 hours. The mixture is cooled to room temperature, diluted with 10 ml. of water and extracted with ether. The aqueous phase is separated and acidified with 6N hydrochloric acid. The precipitated produce is filtered, dried and sublimed at 125° C. and .05 mm pressure, m.p. 143°–145° C.

* Hauptschein, et al., J. Am. Chem. Soc., 76, 1053 (1954).

Anal. Calcd. for $C_{15}H_{11}O_{F3}$: C, 60.81; H, 3.74. Found: C, 60.80; H, 3.70.

EXAMPLE 6

Starting with the requisite reagents, and employing the procedure of Example 4 or Example 5, the following benzoic acids are prepared:

| $R_1$ | Position of Substituent —$OR_1$ | Procedure |
|---|---|---|
| $4\text{-}FC_6H_4CH_2-$ | 2 | Example 4 |
| $3\text{-}FC_6H_4CH_2-$ | 2 | Example 4 |
| $3\text{-}FC_6H_4CH_2-$ | 3 | Example 5 |
| $4\text{-}ClC_6H_4CH_2-$ | 2 | Example 4 |
| $4\text{-}ClC_6H_4CH_2-$ | 4 | Example 4 |
| $2\text{-}ClC_6H_4CH_2-$ | 4 | Example 4 |
| $4\text{-}BrC_6H_4CH_2-$ | 2 | Example 4 |
| $3\text{-}BrC_6H_4CH_2-$ | 3 | Example 5 |
| $4\text{-}CH_3C_6H_4CH_2-$ | 2 | Example 4 |
| $2\text{-}CH_3C_6H_4CH_2-$ | 3 | Example 5 |
| $4\text{-}CH_3OC_6H_4CH_2-$ | 2 | Example 5 |
| $4\text{-}CH_3OC_6H_4CH_2-$ | 6 | Example 4 |
| $3,4\text{-}(CH_3O)_2C_6H_3CH_2-$ | 2 | Example 4 |
| $3,4\text{-}(CH_3O)_2C_6H_3CH_2-$ | 3 | Example 5 |
| $3,4\text{-}(CH_3O)_2C_6H_3CH_2-$ | 4 | Example 4 |
| $3\text{-}CF_3C_6H_4CH_2-$ | 2 | Example 4 |
| $3\text{-}CF_3C_6H_4CH_2-$ | 3 | Example 5 |
| $C_6H_5CH_2-$ | 6 | Example 4 |

EXAMPLE 7

2Benzyloxy-5-methoxybenzoic Acid

A solution of 5.0 g. (0.03 mole) of 2-hydroxy-5-methoxybenzoic acid in 50 ml. of dimethylformamide is treated with 2.5 g. (0.06 mole) of sodium hydride in a 56.6% oil suspension, followed by the addition of 7.6 g. (0.06 mole) of benzyl chloride. The resulting mixture is heated at 98°–103° C. for one hour, after which the insolubles are filtered, the filtrate diluted with 100 ml. of water and the aqueous solution extracted with ether. The aqueous phase is discarded and the ether phase dried over sodium sulfate and evaporated to provide the intermediate, benzyl 2-benzyloxy-5-methoxybenzoate, as an oil, 5.0 g.

The intermediate ester is dissolved in 35 ml. of ethanol containing 30 ml. of 1N aqueous sodium hydroxide solution and the resulting solution heated for 50 minutes on a steam bath. The ethanol is removed in vacuo and the mixture diluted with 20 ml. of water and extracted with ether. The water phase is acidified with12N hydrochloric acid and the product extracted into ether. The ether is evaporated and the residual crude product is chromatographed over 40 g. of Silica Gel packed in ethyl acetate. The desired product is eluted with 100 ml. of ethyl acetate, 2.9 g., m.p. 88°–92° C. and is finally recrystallized from methylene chloride-ether, 1.6 g., m.p. 93°–94.5° C.

Anal. Calcd. for $C_{15}H_{14}O_4$: C, 69.75; H, 5.46. Found: C, 69.65; H, 5.59.

EXAMPLE 8

Employing the procedure of Example 7 and starting with the appropriate chemical reagents, the following analogs are synthesized:

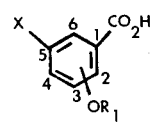

| X | $R_1$ | Position of Substituent —$OR_1$ |
|---|---|---|
| $CH_3$ | $C_6H_5CH_2$— | 2 |
| $CH_3$ | $C_6H_5CH_2$— | 3 |
| $CH_3$ | 4-$FC_6H_4CH_2$— | 2 |
| $CH_3$ | 4-$FC_6H_4CH_2$— | 4 |
| $CH_3$ | 3-$ClC_6H_4CH_2$— | 4 |
| $CH_3$ | 3-$ClC_6H_4CH_2$— | 6 |
| $CH_3$ | 4-$BrC_6H_4CH_2$— | 3 |
| $CH_3$ | 3-$CF_3C_6H_4CH_2$— | 3 |
| $CH_3$ | 3,4-$(CH_3O)_2C_6H_3CH_2$— | 2 |
| $CH_3$ | 3,4-$(CH_3O)_2C_6H_3CH_2$— | 3 |
| $CH_3O$ | $C_6H_5CH_2$— | 3 |
| $CH_3O$ | $C_6H_5CH_2$— | 6 |
| $CH_3O$ | 3-$FC_6H_4CH_2$— | 2 |
| $CH_3O$ | 4-$FC_6H_4CH_2$— | 4 |
| $CH_3O$ | 2-$ClC_6H_4CH_2$— | 2 |
| $CH_3O$ | 4-$ClC_6H_4CH_2$— | 2 |
| $CH_3O$ | 4-$BrC_6H_4CH_2$— | 3 |
| $CH_3O$ | 3-$CF_3C_6H_4CH_2$— | 2 |
| $CH_3O$ | 4-$CF_3C_6H_4CH_2$— | 6 |
| $CH_3O$ | 4-$CH_3C_6H_4CH_2$— | 2 |
| $CH_3O$ | 2-$CH_3C_6H_4CH_2$— | 2 |
| $CH_3O$ | 4-$CH_3OC_6H_4CH_2$— | 2 |
| $CH_3O$ | 4-$CH_3OC_6H_4CH_2$— | 3 |
| $CH_3O$ | 3,4-$(CH_3O)_2C_6H_3CH_2$— | 2 |
| $CH_3O$ | 3,4-$(CH_3O)_2C_6H_3CH_2$— | 3 |

EXAMPLE 9

2-Acetonyloxy-5-chlorobenzoic Acid

To a solution of 5.16 g. (0.3 mole) of 5-chlorosalicylic acid in 60 ml. of ethanol and 40 ml. of water containing 1.2 g. (0.03 mole) of sodium hydroxide is added 2.8 g. (0.03 mole) of chloroacetone and the solution heated to reflux for 5 hours. The resulting solution is cooled in an ice bath and the precipitated product filtered, dried and recrystallized from ether, 800 mg., m.p. 90°–91° C.

Anal. Calcd. for $C_{10}H_9O_4Cl$: C, 52.53; H, 3.97. Found: C, 52.84; H, 4.04.

EXAMPLE 10

In a similar manner, employing the requisite starting materials and following the procedure of Example 11, the following compounds are prepared:

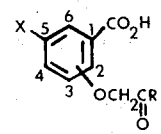

| X | R | Position of Substituent —$OCH_2\overset{O}{\overset{\|}{C}}R$ |
|---|---|---|
| F | $CH_3$— | 2 |
| F | $C_2H_5$— | 2 |
| F | $C_2H_5$— | 3 |
| F | n-$C_3H_7$— | 3 |
| F | i-$C_3H_7$— | 4 |
| F | n-$C_4H_9$— | 6 |
| Cl | $CH_3$— | 2 |
| Cl | $CH_3$— | 3 |
| Cl | n-$C_3H_7$— | 3 |
| Cl | i-$C_3H_7$— | 3 |
| Cl | s-$C_4H_9$— | 4 |
| Cl | n-$C_4H_9$— | 6 |
| Br | $C_2H_5$— | 2 |
| Br | $C_2H_5$— | 4 |
| Br | i-$C_3H_7$— | 2 |
| Br | n-$C_3H_7$— | 2 |
| $CH_3$ | $CH_3$— | 2 |
| $CH_3$ | $CH_3$— | 6 |
| $CH_3$ | t-$C_4H_9$— | 2 |
| $CH_3$ | n-$C_4H_9$— | 4 |
| $CH_3$ | s-$C_4H_9$— | 6 |
| $OCH_3$ | $C_2H_5$— | 2 |
| $OCH_3$ | n-$C_3H_7$— | 3 |
| $OCH_3$ | n-$C_4H_9$— | 3 |
| $OCH_3$ | s-$C_4H_9$— | 6 |
| $CF_3$ | $CH_3$— | 3 |
| $CF_3$ | $C_2H_5$— | 3 |
| $CF_3$ | i-$C_3H_7$— | 3 |
| $CF_3$ | n-$C_4H_9$— | 3 |

EXAMPLE 11

3Phenacyloxy-5-trifluoromethylbenzoic Acid

To 206 mg. (1 m mole) of 3-hydroxy-5-trifluoromethylbenzoic acid dissolved in 2.5 ml. of dimethylsulfoxide is added 85 mg. (2 m moles) of a 56.6% sodium hydride suspension in oil. When the hydrogen evolution has ceased, 199 mg. (1 m mole) of α-bromoacetophenone is added and the reaction mixture is allowed to stir at room temperature for 2 hours. The reaction is diluted with 10 ml. of water and extracted with ether. The aqueous phase is acidified and the product extracted with ether. Removal of the ether under reduced pressure followed by sublimation at 150° C. and 0.1 mm pressure provided the pure product, m.p. 180°–182° C.

Anal. Calcd. for $C_{16}H_{11}O_4F_3$: C, 59.26; H, 3.42. Found: C, 59.26; H, 3.60.

EXAMPLE 12

The procedure of Example 11 is repeated, starting with the appropriate hydroxybenzoic acid and phenacyl halide to provide the following compounds: 2-phenacyloxy-5-fluorobenzoic acid, 2-(4'-fluorophenacyloxy)-5-fluorobenzoic acid, 2-(2'-chlorophenacyloxy)-5-fluorobenzoic acid, 3-(4'-methylphenacyloxy)-5-fluorobenzoic acid, 4-(4'-methylphenacycloxy)-5-chlorobenzoic acid, 3-(4'-methoxyphenacyloxy)-5-chlorobenzoic acid, 3-(4'-methoxyphenacyloxy)-5-chlorobenzoic acid, 3-(4'-fluorophenacyloxy)-5-bromobenzoic acid, 2-phenacyloxy-5-bromobenzoic acid, 3-(2'-methylphenacyloxy)-5-trifluoromethylbenzoic acid, 3-((4'-methoxyphenacyloxy)-5-trifluoromethylbenzoic acid, 3-(3'-trifluoromethylphenacyloxy)-5-trifluoromethylbenzoic acid, 4-(4'-fluorophenacyloxy)-5-methylbenzoic acid, 6-(3'-methoxyphenacyloxy)-5-methylbenzoic acid, 4-(2'-methoxyphenacyloxy)-5-methylbenzoic acid, 2-(4'-fluorophenacyloxy)-5-methoxybenzoic acid, 3-(3'-chlorophenacyloxy)-5-methoxybenzoic acid, 6-(4'-methoxyphenacyloxy)-5-methoxybenzoic acid, 2-(3'-trifluoromethylphenacyloxy)-5-methoxybenzoic acid and 3-phenacyloxy-5-methoxybenzoic acid.

EXAMPLE 13

2-Methylthio-5-trifluoromethylbenzoic Acid

Into 75 ml. of dimethylformamide containing 20 ml. of 5N sodium hydroxide solution is bubbled methyl mercaptan until a weight increase of 6.3 g. (~30% excess) is noted, followed by the addition of 20.5 g. (0.1 mole) of 4-chloro-3-cyanobenzotrifluoride. After allowing the reaction mixture to stir at room temperature for 2 hours, the precipitated solid is filtered and the filtrate diluted with 500 ml. of water and extracted with ether. The ether layer is separated, dried over sodium sulfate and concentrated to a semi-solid which on trituration with hexane provides the desired intermediate, 4-methylthio-3-cyanobenzotrifluoride, as a crystalline solid, 15.2 g., m.p. 68°–72° C.

Thirteen grams of the above intermediate in 150 ml. of ethanol containing 200 ml. of 20% aqueous sodium hydroxide solution is heated at 90° C. for 18 hours. The reaction mixture is cooled and acidified with 12N hydrochloric acid, and the resulting precipitate filtered and dried, 14.2 g., m.p. 198°–200° C. A small sample is sublimed at 125°–135° C. and 0.02 mm pressure, m.p. 198.5–200° C.

Anal. Calcd. for $C_9H_7O_2SF_3$: C, 45.76; H, 2.99. Found: C, 46.09; H, 3.10.

In a similar manner are prepared: 2-(2-hydroxyethylthio)-5-trifluoromethylbenzoic acid, m.p. 153°–154° C.; 2-crotylthio-5-trifluoromethylbenzoic acid, m.p. 139°–141° C.; 2-methallythio-5-trifluoromethylbenzoic acid, m.p. 150°–152° C. and 2-allythio-5-trifluoromethylbenzoic acid, m.p. 178°–190° C.

EXAMPLE 14

3-Methylthio-5-trifluoromethylbenzoic Acid

To a solution of 10 g. (0.045 mole) of 3-mercapto-5-trifluoromethylbenzoic acid, and 100 ml. of 1N sodium hydroxide in 100 ml. of ethanol is added 3.8 ml. (0.06 mole) of methyl iodide. After the reaction has stirred at room temperature for one hour, it is acidified with 12N hydrochloric acid, and the precipitate of the final product is filtered and dried, 8.6 g., m.p. 135°–140° C. A sample is sublimed at 175° C. and 0.03 mm pressure, m.p. 151°–152.5° C.

Anal. Calcd. for $C_9H_7O_2SF_3$: C, 45.76; H, 2.99. Found: C, 45.85; H, 3.02.

EXAMPLE 15

Following the procedure of Example 13 or Example 14, and starting with the requisite chemical reagents, the following congeners are synthesized:

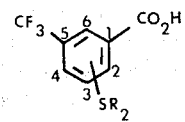

| $R_2$ | Position of Substituent —$SR_2$ | Procedure |
|---|---|---|
| $CH_3$— | 4 | Example 13 |
| $CH_3$— | 6 | Example 13 |
| $CH_2=CH—CH_2$— | 3 | Example 14 |
| $CH_2=CH—CH_2$— | 4 | Example 13 |
| $CH_3CH=CH—CH_2$— | 3 | Example 14 |
| $CH_3CH=CH—CH_2$— | 6 | Example 13 |
| $CH_2=C(CH_3)CH_2$— | 3 | Example 14 |
| $CH_2=C(CH_3)CH_2$— | 4 | Example 13 |
| $CH_2=C(CH_3)CH_2$— | 6 | Example 13 |
| $HOCH_2CH_2$— | 3 | Example 14 |
| $HOCH_2CH_2$— | 6 | Example 13 |

EXAMPLE 16

3-Methylthio-5-chlorobenzoic Acid

In a manner similar to procedure of Example 14, 3-mercapto-5-chlorobenzoic acid is contacted with methyl iodide in methanol containing potassium hydroxide as the base to yield the desired product in 70% yield, m.p. 148°–150° C.

Anal. Calcd. for $C_8H_7O_2SCl$: C, 47.41; H, 3.48. Found: C, 47.55; H, 3.56.

EXAMPLE 17

Again, the procedure of Example 14 is employed, starting with the appropriate starting reagents to provide the following analogs:

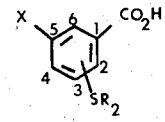

| X | $R_2$ | Position of Substituent —$SR_2$ |
|---|---|---|
| F | $CH_3$— | 2 |
| F | $CH_3$— | 4 |
| F | $CH_2=CH—CH_2$— | 3 |
| F | $CH_3CH=CH—CH_2$— | 3 |
| F | $CH_3CH=CH—CH_2$— | 4 |
| F | $HOCH_2CH_2$— | 3 |
| Cl | $CH_3$— | 2 |
| Cl | $CH_2=C(CH_3)CH_2$— | 2 |
| Cl | $CH_2=C(CH_3)CH_2$— | 3 |
| Cl | $CH_2=C(CH_3)CH_2$— | 6 |
| Cl | $HOCH_2CH_2$— | 2 |
| Br | $CH_3$— | 2 |

-continued

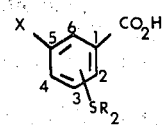

| X | $R_2$ | Position of Substituent $-SR_2$ |
|---|---|---|
| Br | $CH_3-$ | 3 |
| Br | $CH_3-$ | 4 |
| Br | $HOCH_2CH_2-$ | 2 |
| Br | $CH_2=CH-CH_2-$ | 2 |
| $CH_3$ | $CH_3-$ | 2 |
| $CH_3$ | $CH_3-$ | 6 |
| $CH_3$ | $CH_3CH=CH-CH_2-$ | 2 |
| $CH_3$ | $CH_2=C(CH_3)CH_2-$ | 2 |
| $CH_3$ | $HOCH_2CH_2-$ | 2 |
| $CH_3O$ | $CH_3-$ | 2 |
| $CH_3O$ | $CH_2=CH-CH_2-$ | 3 |
| $CH_3O$ | $CH_2=CH-CH_2-$ | 4 |
| $CH_3O$ | $CH_2=CH-CH_2-$ | 6 |
| $CH_3O$ | $CH_3CH=CH-CH_2-$ | 2 |
| $CH_3O$ | $CH_3CH=CH-CH_2-$ | 3 |

EXAMPLE 18

2-Phenacylthio-5-trifluoromethylbenzoic Acid

A suspension of 14 g. (0.06 mole) of methyl 2-chloro-5-trifluorobenzoate, 9.0 g. (0.06 mole) of $\alpha$-mercaptoacetophenone and 4.2 g. (0.03 mole) of potassium carbonate in 45 ml. of dimethylformamide is allowed to stir at room temperature for 3 hours after which 200 ml. of ether is added and the resulting mixture extracted with water. The ether layer is separated, dried over sodium sulfate and concentrated to an oil, which crystallizes on treatment with isopropyl ether, 1.6 g., m.p. 128.5°–130° C. The analytical sample of the intermediate, methyl 2-phenacylthio-5-trifluoromethylbenzoate, is purified by sublimation at 120° C. and 0.01 mm pressure, m.p. 127°–129° C.

Anal. Calcd. for $C_{17}H_{13}O_3SF_3$: C, 57.62; H, 3.70. Found: C, 57.66; H, 3.70.

The desired acid is prepared from the crude ester through mild base hydrolysis.

EXAMPLE 19

3-Phenacylthio-5-trifluoromethylbenzoic Acid

A mixture of 1.33 g. (6 m moles) of 3-mercapto-5-trifluoromethylbenzoic acid, 12 ml. of 1N sodium hydroxide solution and 930 mg. (6 m moles) of $\alpha$-chloroacetophenone in 20 ml. of ethanol is allowed to stir at room temperature for 1 hour. The reaction mixture is diluted with water, extracted with ether and the resulting aqueous phase acidified with 12N hydrochloric acid. The light yellow oil which separates gradually crystallizes and is filtered, 1.8 g., m.p. 135°–150° C. A sample is sublimed at 165° C. and 0.05 mm pressure, m.p. 153°–155° C.

Anal. Calcd. for $C_{16}H_{11}O_3SF_3$: C, 56.47; H, 3.26. Found: C, 56.84; H, 2.88.

EXAMPLE 20

Employing the procedure of Example 18 or Example 19, and starting with the appropriate reagents, the following benzoic acid derivatives are prepared:

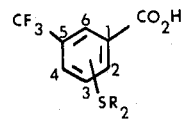

| $R_2$ | Position of Substituent $-SR_2$ | Procedure |
|---|---|---|
| $CH_3\overset{O}{\overset{\|}{C}}CH_2-$ | 3 | Example 19 |
| $C_2H_5\overset{O}{\overset{\|}{C}}CH_2-$ | 3 | Example 19 |
| $(CH_3)_2CH\overset{O}{\overset{\|}{C}}CH_2-$ | 4 | Example 18 |
| $C_6H_5\overset{O}{\overset{\|}{C}}CH_2-$ | 4 | Example 18 |
| $C_6H_5\overset{O}{\overset{\|}{C}}CH_2-$ | 6 | Example 18 |
| $4\text{-}FC_6H_4\overset{O}{\overset{\|}{C}}CH_2-$ | 3 | Example 19 |
| $4\text{-}FC_6H_4\overset{O}{\overset{\|}{C}}CH_2-$ | 6 | Example 18 |
| $3\text{-}ClC_6H_4\overset{O}{\overset{\|}{C}}CH_2-$ | 2 | Example 18 |
| $4\text{-}ClC_6H_4\overset{O}{\overset{\|}{C}}CH_2-$ | 3 | Example 19 |
| $4\text{-}CH_3C_6H_4\overset{O}{\overset{\|}{C}}CH_2-$ | 3 | Example 19 |
| $3\text{-}CH_3OC_6H_4\overset{O}{\overset{\|}{C}}CH_2-$ | 3 | Example 19 |
| $4\text{-}CH_3OC_6H_4\overset{O}{\overset{\|}{C}}CH_2-$ | 3 | Example 19 |
| $4\text{-}CH_3OC_6H_4\overset{O}{\overset{\|}{C}}CH_2-$ | 6 | Example 18 |
| $3\text{-}CF_3C_6H_4\overset{O}{\overset{\|}{C}}CH_2-$ | 3 | Example 19 |

EXAMPLE 21

2-Phenacylthio-5-chlorobenzoic Acid

A solution of 18.9 g. (0.1 mole) of 5-chlorothiosalicylic acid, 15.4 g. (0.1 mole) of $\alpha$-chloroacetophenone and 8 g. (0.2 mole) of sodium hydroxide in 200 ml. of ethanol containing 45 ml. of water is heated to reflux for 2 hours. After removing one-fourth the alcohol under reduced pressure, the mixture is acidified with hydrochloric acid and the resulting precipitated product filtered, 5.0 g., m.p. 154°–156° C. The analytical sample has a melting point of 156°–157.5° C.

Anal. Calcd. for $C_{15}H_{11}O_3SCl$: C, 58.72; H, 3.62. Found: C, 58.59; H, 3.74.

EXAMPLE 22

In a similar manner to the procedure of Example 21, but substituting chloroacetone for chloroacetophenone, the corresponding 2-acetonylthio-5-chlorobenzoic acid is prepared, m.p. 139°–140° C.

Anal. Calcd. for $C_{10}H_9O_3SCl$: C, 49.08; H, 3.71. Found: C, 49.21; H, 3.80.

EXAMPLE 23

Starting with the appropriate chemical reagents and following the procedure of Example 21, the following benzoic acids are prepared:

2-acetonylthio-5-fluorobenzoic acid, 4-phenacylthio-3-fluorobenzoic acid, 3-(4'-fluorophenacylthio)-5-fluorobenzoic acid, 3-(4'-methoxyphenacylthio)-5-fluorobenzoic acid, 2-(3'-methylphenacylthio)-5-chlorobenzoic acid, 2-(4'-methoxyphenacylthio)-5-chlorobenzoic acid, 3(3'-trifluoromethylphenacylthio)-5-chlorobenzoic acid, 3-acetonylthio-5-chlorobenzoic acid, 2-isobutyrylmethylthio-5-chlorobenzoic acid, 2-acetonnylthio-5-bromobenzoic acid, 3-(4'-methoxyphenacylthio)-5-bromobenzoic acid, 4-(3'-trifluoromethylphenacylthio)-5-bromobenzoic acid, 2-(4'-chlorphenacylthio)-5-bromobenzoic acid, 2-acetonylthio-5-methylbenzoic acid, 2-phenacylthio-5-methylbenzoic acid, 2-(4'-fluorophenacylthio)-3-methylbenzoic acid, 2-(4'-methoxyphenacylthio)-5-methylbenzoic acid, 2-acetonylthio-5-methoxybenzoic acid, 3-phenacylthio-5-methoxybenzoic acid, 2-(4'-chlorophenacylthio)-5-methoxybenzoic acid, 2-(4'-methylphenacylthio)-3-methoxybenzoic acid and 3-(3'-trifluoromethylphenacylthio)-5-methhoxybenzoic acid.

EXAMPLE 24

3-Phenacylsulfinyl-5-trifluoromethylbenzoic Acid

A solution of 2.6 g. (7.5 m moles) of 3-phenacylthio-5-trifluoromethylbenzoic acid and .75 ml. of 30% hydrogen peroxide in 15 ml. of acetic acid is heated on a steam bath for 1 hour, after which the reaction mixture is cooled and diluted with water to the turbidity point. The crystalline product which forms on standing is filtered, 1.0 g., m.p. 148°–151° C., and finally recrystallized from acetone-isopropyl ether, 850 mg., m.p. 154°–155° C.

Anal. Calcd. for $C_{16}H_{11}O_4SF_3$: C, 53.93; H, 3.11. Found: C, 54.11; H, 3.29.

EXAMPLE 25

2-Phenacylsulfonyl-5-chlorobenzoic Acid

In a manner similar to the procedure of Example 24, 1.0 g. (3 m moles) of 2-phenacylthio-5-chlorobenzoic acid and 3 ml. of 30% hydrogen peroxide in 40 ml. of acetic acid yielded 800 mg. of the desired sulfone, m.p. 170°–171° C.

Anal. Calcd. for $C_{15}H_{11}O_5SCl$: C, 53.18; H, 3.27. Found: C, 53.16; H, 3.32.

EXAMPLE 26

The following sulfoxides and sulfones are prepared, starting with the requisite chemicals, by repeating the procedure of Examples 24 and 25 respectively:

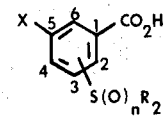

| X | $R_2$ | n | Position |
|---|---|---|---|
| $CF_3$ | $CH_3-$ | 1 | 2 |
| $CF_3$ | $HOCH_2CH_2-$ | 1 | 2 |
| $CF_3$ | $HOCH_2CH_2-$ | 2 | 2 |
| $CF_3$ | $CH_2=CH-CH-$ | 1 | 2 |
| $CF_3$ | $CH_3-$ | 2 | 4 |
| F | $CH_3-$ | 1 | 4 |
| F | $CH_3-$ | 2 | 4 |
| F | $CH_3CH=CH-CH_2-$ | 2 | 3 |
| F | $HOCH_2CH_2-$ | 1 | 3 |
| Cl | $CH_3-$ | 1 | 2 |
| Cl | $CH_3-$ | 2 | 2 |
| Cl | $CH_2=C(CH_3)CH_2-$ | 1 | 6 |
| Cl | $CH_2=C(CH_3)CH_2-$ | 1 | 3 |
| Br | $CH_3-$ | 2 | 2 |
| Br | $CH_3-$ | 2 | 3 |
| Br | $HOCH_2CH_2-$ | 1 | 2 |
| Br | $HOCH_2CH_2-$ | 2 | 2 |
| $CH_3$ | $CH_2=C(CH_3)CH_2-$ | 1 | 2 |
| $CH_3$ | $CH_3CH=CHCH_2-$ | 2 | 2 |
| $OCH_3$ | $CH_2=CHCH_2-$ | 1 | 3 |
| $OCH_3$ | $CH_2=CHCH_2-$ | 2 | 3 |
| $OCH_3$ | $CH_2=CHCH_2-$ | 1 | 4 |
| $OCH_3$ | $CH_3CH=CHCH_2-$ | 1 | 3 |
| $OCH_3$ | $CH_3CH=CHCH_2-$ | 2 | 3 |
| $CF_3$ | $C_6H_5\overset{O}{\underset{\|}{C}}CH_2-$ | 2 | 3 |
| $CF_3$ | $C_2H_5\overset{O}{\underset{\|}{C}}CH_2-$ | 1 | 3 |
| $CF_3$ | $C_2H_5\overset{O}{\underset{\|}{C}}CH_2-$ | 2 | 3 |
| $CF_3$ | $4\text{-}FC_6H_4\overset{O}{\underset{\|}{C}}CH_2-$ | 1 | 6 |
| $CF_3$ | $3\text{-}ClC_6H_4\overset{O}{\underset{\|}{C}}CH_2-$ | 1 | 2 |
| $CF_3$ | $3\text{-}ClC_6H_4\overset{O}{\underset{\|}{C}}CH_2-$ | 2 | 2 |
| $CF_3$ | $3\text{-}CH_3OC_6H_4\overset{O}{\underset{\|}{C}}CH_2-$ | 1 | 3 |
| $CF_3$ | $3\text{-}CF_3C_6H_4\overset{O}{\underset{\|}{C}}CH_2-$ | 2 | 3 |
| F | $CH_3\overset{O}{\underset{\|}{C}}CH_2-$ | 2 | 2 |
| F | $C_6H_5\overset{O}{\underset{\|}{C}}CH_2-$ | 2 | 4 |
| F | $4\text{-}CH_3OC_6H_4\overset{O}{\underset{\|}{C}}CH_2-$ | 1 | 3 |
| Cl | $3\text{-}CH_3C_6H_4\overset{O}{\underset{\|}{C}}CH_2-$ | 1 | 2 |
| Cl | $3\text{-}CH_3C_6H_4\overset{O}{\underset{\|}{C}}CH_2-$ | 2 | 2 |
| Cl | $4\text{-}CH_3OC_6H_4\overset{O}{\underset{\|}{C}}CH_2-$ | 2 | 2 |

-continued

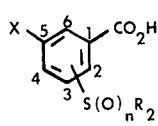

| X | R₂ | n | Position |
|---|---|---|---|
| Cl | CH₃C(O)CH₂— | 1 | 3 |
| Cl | CH₃C(O)CH₂— | 2 | 3 |
| Br | 4-CH₃OC₆H₄C(O)CH₂— | 2 | 3 |
| Br | 3-CH₃C₆H₄C(O)CH₂— | 1 | 4 |
| Br | 4-ClC₆H₄C(O)CH₂— | 2 | 2 |
| CH₃ | 2-C₆H₅C(O)CH₂— | 2 | 2 |
| CH₃ | CH₃C(O)CH₂— | 1 | 2 |
| CH₃ | CH₃C(O)CH₂— | 2 | 2 |
| CH₃ | 4-FC₆H₄C(O)CH₂— | 1 | 2 |
| CH₃O | CH₃C(O)CH₂— | 1 | 2 |
| CH₃O | C₆H₅C(O)CH₂— | 2 | 3 |
| CH₃O | 4-ClC₆H₄C(O)CH₂— | 1 | 2 |
| CH₃O | 4-ClC₆H₄C(O)CH₂— | 2 | 2 |

EXAMPLE 27

3Methoxy-5-trifluoromethylbenzoic Acid

This product is prepared according to the procedure of Example 5 and comprises contacting 3-hydroxy-5-trifluoromethylbenzoic acid with methyl iodide in methanol containing sodium methoxide as the base, m.p. 131°–135° C.

Anal. Calcd. for $C_9H_7O_3F_3$: C, 49.11; H, 3.20. Found: C, 49.28; H, 3.30.

EXAMPLE 28

2-Methoxy-5-trifluoromethylbenzoic Acid

Starting with 4-chloro-3-cyanobenzotrifluoride and sodium methoxide and following the procedure of Example 4, the above product is prepared, m.p. 105°–106.5° C. Netherlands Application 6,507,712 (C.A., 64, 12606g) reports a melting point of 103°–105° C. for this compound.

In a similar manner are prepared 2-methoxy-3-trifluoromethylbenzoic acid and 3-trifluoromethyl-4-methoxybenzoic acid.

EXAMPLE 29

Groups, each comprising 4 animals, of normal Sprague-Dawley Charles River) male rats weighing from 160 to 220 grams are fed rat chow containing the test compounds for two overnight feeding periods. On the morning of the third day the animals are anesthetized and bled from the abdominal aorta. The total plasma cholesterol is then determined by the method of J. J. Carr and I. J. Drekter reported in Clin. Chem., 2, 353 (1956). Most of the tests are conducted at a concentration in the feed of 0.15 to 0.25 weight percent of the compound under test, but lower levels are employed in some instances. the total quantity of test compound consumed is computed from feed consumption over the two-day period and is tabulated, in milligrams per kilogram body weight per day, along with the associated percent cholesterol fall measured:

| Compound | % Cholesterol Fall | Daily Dosage mg./kg. |
|---|---|---|
| 2-Methoxy-5-trifluoromethylbenzoic acid | 42 | 223 |
| 2-Benzyloxy-5-trifluoromethylbenzoic acid | 41 | 256 |
| 2-Chloro-5-trifluoromethylbenzoic acid | 19 | 231 |
| 2-Benzyloxy-5-chlorobenzoic acid | 17 | 208 |
| 3-Benzyloxy-5-trifluoromethylbenzoic acid | 18 | 164 |
| 2-Methoxy-5-chlorobenzoic acid | 28 | 217 |
| 3-Methoxy-5-trifluoromethylbenzoic acid | 48 | 214 |
| 2-Acetonyloxy-5-chlorobenzoic acid | 32 | 158 |
| 2-(4'-Chlorobenzyloxy)-5-chlorobenzoic acid | 14 | 240 |
| 2-Methoxy-4-trifluoromethylbenzoic acid | 39 | 227 |
| 3-Benzyloxy-5-chlorobenzoic acid | 20 | 178 |
| 2-Benzyloxy-5-methoxybenzoic acid | 17 | 242 |
| 2-(3',4'-Dimethoxybenzyloxy)-5-chlorobenzoic acid | 36 | 227 |
| 2,5-Dimethoxybenzoic acid | 20 | 243 |
| 3-Chloro-5-trifluoromethylbenzoic acid | 13 | 141 |
| 2-Bromo-5-trifluoromethylbenzoic acid | 15 | 140 |
| 2,4-Dichlorobenzoic acid | 42 | 149 |
| 2-Bromo-5-chlorobenzoic acid | 16 | 106 |
| 2-Methylthio-5-trifluoromethylbenzoic acid | 27 | 255 |
| 2-Methylsulfinyl-5-trifluoromethylbenzoic acid | 14 | 265 |
| 2-Allylthio-5-trifluoromethylbenzoic acid | 40 | 185 |

| Compound | % Cholesterol Fall | Daily Dosage mg./kg. |
|---|---|---|
| 2-Phenacylthio-5-chlorobenzoic acid | 31 | 219 |
| 2-Phenacylsulfonyl-5-chlorobenzoic acid | 21 | 233 |
| 3-Phenacylthio-5-trifluoromethylbenzoic acid | 20 | 229 |
| 3-Phenacylsulfinyl-5-trifluormethylbenzoic acid | 20 | 247 |
| 3-Methylsulfonyl-5-trifluoromethylbenzoic acid | 13 | 255 |
| 2-(2'-Hydroxyethylthio)-5-trifluoromethyl-benzoic acid | 22 | 253 |
| 2-(2'-Hydroxyethylthio)-5-chlorobenzoic acid | 29 | 245 |
| 2-Acetonylthio-5-chlorobenzoic acid | 21 | 229 |
| 2-Crotylthio-5-trifluoromethylbenzoic acid | 16 | 255 |
| 2-Methallylthio-5-trifluoromethylbenzoic acid | 25 | 244 |
| 3-Methylthio-5-chlorobenzoic acid | 22 | 199 |
| 3-Fluorobenzoic acid | 0 | 228 |
| 5-Chloro-2-(4'-chlorophenylureylene)benzoic acid | 32 | 249 |
| 5-Trifluoromethyl-2-benzylaminobenzoic acid | 17 | 148 |
| 5-Chloro-2-(n-propylureylene)benzoic acid | 10 | 199 |
| 5-Trifluoromethyl-2-(3-methylpiperidino)-benzoic acid | 27 | 196 |
| 5-Trifluoromethyl-2-(3,5-dimethylpiperidino)-benzoic acid | 19 | 144 |
| 5-Trifluoromethyl-2-acetamidobenzoic acid | 7 | 127 |
| 5-Trifluoromethyl-2-benzamidobenzoic acid | 26 | 128 |
| 5-Trifluoromethyl-2-diethylaminobenzoic acid | 6 | 141 |

In a similar manner, when tested by the above procedure, the following benzoic acids also lower cholesterol levels: 3,5-difluorobenzoic acid, 2,5-difluorobenzoic acid, 2-chloro-5-fluorobenzoic acid, 3-fluoro-4-chlorobenzoic acid, 3-fluoro-4-bromobenzoic acid, 2,3-dibromobenzoic acid, 2-bromo-5-fluorobenzoic acid, 3,5-dibromobenzoic acid, 3-fluoro-4-methylbenzoic acid, 2-methyl-5-fluorobenzoic acid, 2,5-dimethylbenzoic acid, 2,3-dimethylbenzoic acid, 2-methylthio-5-fluorobenzoic acid, 2-methylthio-5-methoxybenzoic acid, 3-fluoro-5-trifluorobenzoic acid, 2-methylthio-5-methylbenzoic acid, 3-bromo-5-methoxybenzoic acid, 3-trifluoromethyl-4-methylbenzoic acid, 2-chloro-5-methylbenzoic acid, 2-chloro-5-methylbenzoic acid, 2-methylthio-5-bromobenzoic acid, 3-methyl-5-methoxybenzoic acid, 3-methoxy-4-fluorobenzoic acid, 3-fluoro-5-methoxybenzoic acid, 3-bromo-5-methylbenzoic acid and 3-methyl-4-bromobenzoic acid.

EXAMPLE 30

A dry solid pharmaceutical composition is prepared by combining the following materials in the indicated weight proportions:

| | |
|---|---|
| 2-benzyloxy-5-trifluoromethylbenzoic acid | 50 |
| calcium carbonate | 20 |
| polyethylene glycol, average molecular weight 4000 | 30 |

The dry mixture is thoroughly agitated to obtain a completely uniform blend. Soft elastic and hard gelatin capsules containing this composition are then prepared, employing sufficient material to provide each capsule with 190 mg. of active ingredient.

EXAMPLE 31

A dry solid pharmaceutical composition is prepared by blending the following materials together in the specified weight proportions:

| | |
|---|---|
| 3-methoxy-5-trifluoromethylbenzoic acid | 50 |
| sodium citrate | 25 |
| alginic acid | 10 |
| polyvinylpyrrolidone | 10 |
| magnesium stearate | 5 |

After the dried composition is thoroughly blended, tablets are punched from the mixture, each tablet being of such size as to contain 100 mg. of the active ingredient. Tablets are also prepared containing, respectively, 5, 10, 25 and 50 mg. of the active ingredient, by employing the appropriate proportions of 3-methoxy-5-trifluoromethylbenzoic acid and excipient blend in each case.

EXAMPLE 32

2-Benzyloxy-5-trifluoromethylbenzoic Acid Sodium Salt

To a solution of 400 mg. (0.01 mole) of sodium hydroxide in 30 ml. of water is added, in portions and with stirring, 2.96 g. (0.01 mole) of 2-benzyloxy-5-trifluoromethylbenzoic acid. The slightly hazy solution is filtered and the filtrate concentrated at room temperature and under reduced pressure to dryness. The residual sodium salt is triturated with acetone and filtered.

In a similar manner the products of the present invention are converted to their pharmaceutically acceptable basic salts.

What is claimed is:

1. A method for reducing blood lipid levels which comprises administering to a hyperlipemic mammal a hypolipemic effective amount of a compound selected from the group consisting of

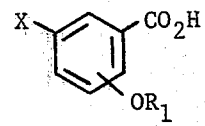

and the pharmaceutically acceptable salts thereof wherein

X is selected from the group consisting of fluorine, chlorine, bromine, methyl, methoxy and trifluoromethyl and $R_1$ is acylmethyl of the formula

wherein R is selected from the group consisting of alkyl having from 1 to 4 carbon atoms and phenyl.
2. The method of claim 1, wherein said compound is of the formula:
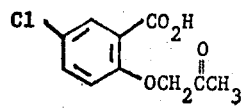
* * * * *